United States Patent [19]

Bills, Jr. et al.

[11] Patent Number: 4,523,475
[45] Date of Patent: Jun. 18, 1985

[54] SIMULTANEOUS INCREMENTAL STRAIN/INCREMENTAL TEMPERATURE ANALOG DEVICE FOR, AND METHOD, OF TESTING FOR STRESS RESPONSE

[75] Inventors: Kenneth W. Bills, Jr., Sacramento; Gerald J. Svob, Fair Oaks, both of Calif.

[73] Assignee: The United States of America as represented by the Secretary of the Air Force, Washington, D.C.

[21] Appl. No.: 533,330

[22] Filed: Sep. 19, 1983

[51] Int. Cl.³ .............................................. G01N 3/00
[52] U.S. Cl. ................................ 73/781; 73/432 SD; 374/49; 374/51
[58] Field of Search ............... 374/46, 49, 51; 73/818, 73/826, 766, 781, 432 SD; 33/DIG. 19

[56] References Cited

U.S. PATENT DOCUMENTS

| | | | |
|---|---|---|---|
| 2,754,675 | 7/1956 | More | 73/15.6 |
| 3,842,654 | 10/1974 | Bechtel | 374/51 |
| 3,902,353 | 9/1975 | San Miguel | 73/15.6 |
| 3,958,176 | 5/1976 | Kraeutle | 324/65 R |
| 3,974,679 | 8/1976 | Nasser | 73/15.6 |

Primary Examiner—Jerry W. Myracle
Attorney, Agent, or Firm—Donald J. Singer; Frank J. Lamattina

[57] ABSTRACT

A device for, and a method of, applying an incremental strain to a test specimen of a solid propellant which is at the stress-free temperature, while simultaneously subjecting the test specimen to an incremental temperature change above and below the stress-free temperature. The device includes a frame assembly in which a captive "strain multiplier" is used to apply the thermally induced loads to the test specimen of the solid propellant that is mounted within the device. Temperature changes, above or below the stress-free temperature, cause volume changes of the rubber members of the "strain multiplier" and result in the "strain multiplier" axially loading the mounted test specimen in simulation of the loading conditions that occur in a case-bonded solid rocket grain. When the temperature is raised, the rubber members expand and exert an axial compressive load on the mounted specimen; and, when the temperature is lowered, the rubber members contract and exert an axial tensile load on the mounted specimen.

22 Claims, 11 Drawing Figures

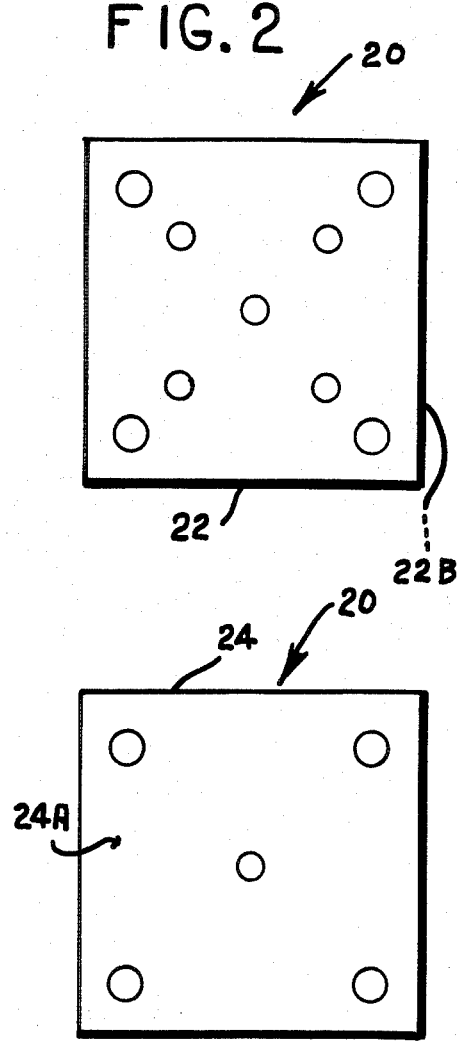
FIG. 2
FIG. 3
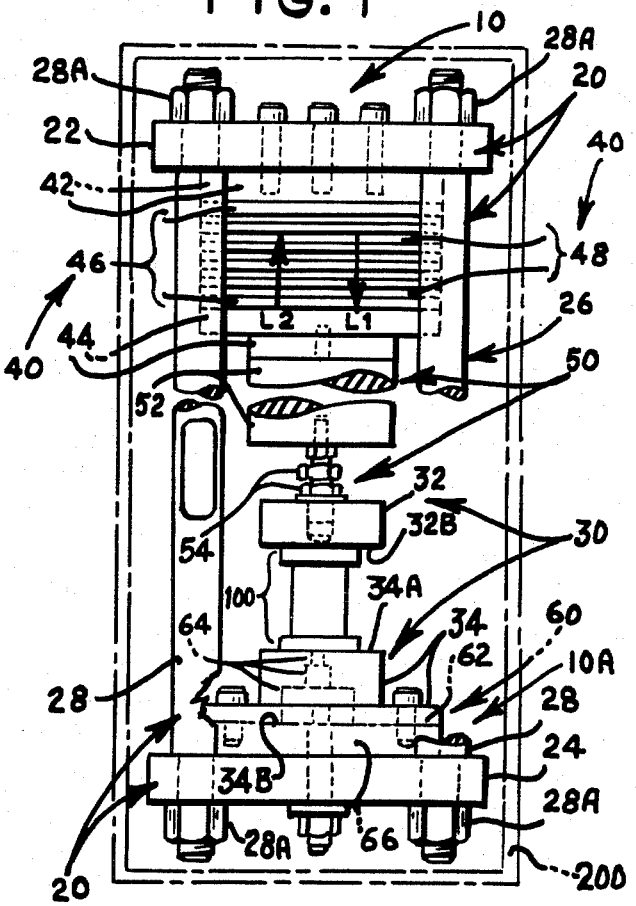
FIG. 1
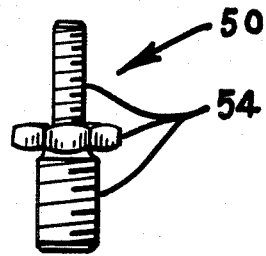
FIG. 7
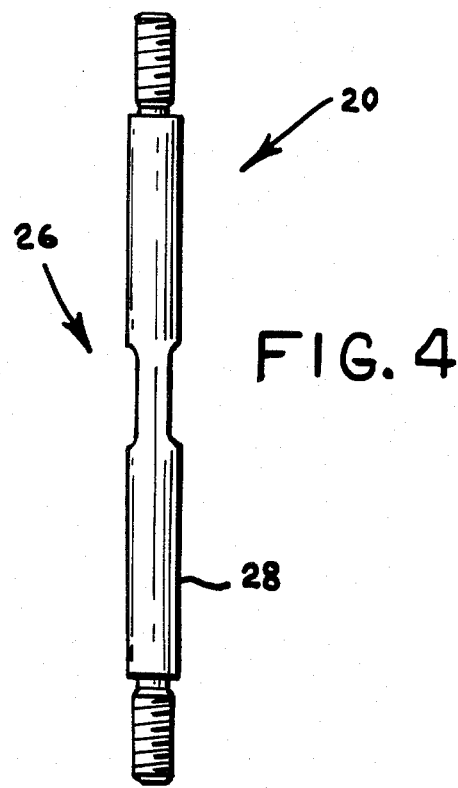
FIG. 4

SIMULTANEOUS INCREMENTAL STRAIN/INCREMENTAL TEMPERATURE ANALOG DEVICE FOR, AND METHOD, OF TESTING FOR STRESS RESPONSE

STATEMENT OF GOVERNMENT INTEREST

The invention described herein may be manufactured and used by or for the Government for governmental purposes without the payment of any royalty thereon.

BACKGROUND OF THE INVENTION

This invention relates generally to the testing art, and more particularly to a unique simultaneous incremental strain/incremental temperature analog drive for, and a method of, testing and evaluating the stress response of a solid propellant under thermally induced loading conditions (i.e., axial compressive or tensile loading) which directly simulate those conditions occurring in a case-bonded solid rocket grain. For those not of the art, it is here to be noted that a solid rocket grain is a configured solid propellant.

The stress-free temperature ($T_{SF}$) of a solid rocket grain is defined as that temperature where thermally induced stresses are zero. For the freshly cured propellant that temperature falls a few degrees above the cure temperature, with the shift being due to a small cure shrinkage. It is standard practice in the art to use the latter temperature as the reference point for all solid rocket grain stress analyses, regardless of the environmental exposures involved. Unfortunately, however, actual laboratory measurements have established that shifts in $T_{SF}$ ranging from 60 percent to 100 percent of the differential between the cure temperature and the storage temperature may not be unusual. The problem assooiated with shifts of this magnitude lies in the fact that any stress analysis of the solid rocket grain, regardless of the level of sophistication of the analysis, will be invalidated if it assumes the solid rocket grain to be stress free at the cure temperature. This is particularly serious if the rocket motor in which the solid propellant grain is incorporated is stored at some elevated temperature, because in such a situation the actual stresses developed during subsequent cooling will be higher than predicted. The shifts to lower temperature, which can occur under temperate or controlled storage conditions, may, upon first consideration, appear to be beneficial, but they could cause unacceptable bond shear stresses to develop upon subsequent heating of the solid rocket grain. Shifts in either direction could cause serious errors in rocket motor life predictions, if not properly taken in account.

In addition to the above, significant shifts in stress-free temperature in a stored rocket motor can completely negate the beneficial effects of motor ambient cure and of high pressure cure. Both of these processing techniques have been used extensively in attempts to reduce the structural requirements imposed on case-bonded solid rocket grains.

If one recognizes the significance of the stress-free temperature shift phenomenon to structural and aging evaluations of a solid propellant, then it becomes readily apparent that what is needed in the art and is not presently available is a laboratory means which will permit reliable measurement of $T_{SF}$ shift behavior. Stated another way, what is needed is an arrangement (i.e., device and/or method) which permits the laboratory evaluation of a preselected solid propellant's stress response under various theormomechanically coupled loading conditions which closely simulate those to which the case-bonded solid rocket grain of that solid propellant is exposed during tactical motor deployment.

SUMMARY OF THE INVENTION

The instant invention satisfies the above-mentioned need in the art. It, therefore, constitutes a significant advance in the state-of-the-art.

The inventive simultaneous incremental strain/incremental temperature analog device is structured for use in a laboratory to produce significant strains in a test specimen of a preselected solid propellant, which is mounted in the analog device, through the application of temperature changes to a unique "strain multiplier" constituent component of the analog device. This "strain multiplier" assembly acts on the mounted test specimen, and it includes a plurality of disk-like (i.e., circular and thin, such as "poker chips") rubber members which are similarly configured, axially aligned, stacked and sandwiched between two metal attachment members. Because of the lateral restraint imposed on the rubber disk members by other components of the analog device, volume changes of the laterally-restrained rubber disk members, which are induced in the rubber disk members by thermal expansion (due to increase in temperature) or thermal contraction (due to decrease in temperature), will be accomodated by movement of each rubber disk member in the axial direction of the analog device. It has been found that the resulting deflections (i.e., upwardly movements with increase in temperature and downwardly movements with decrease in temperature) of the axially-loaded rubber disk members are approximately three (3) times greater than could be realized from unrestrained rubber disk members of the same thickness. Further multiplication of the movement (i.e., of the deflection) can be obtained by using a plurality of the rubber disk members, together with a plurality of metal disk members, such that a metal disk member is positioned between every two adjacent rubber disk members, and a stack of the rubber disk members and of the metal disk members is formed, with a rubber disk member being at the top of the stack, another rubber disk member being at the bottom of the stack, and the stack itself being sandwiched between the two metal attachment members.

The load applied to the solid propellant test specimen by the "strain multiplier" is measured by a load cell interposed between, and operatively associated with, the mounted test specimen and the "strain multiplier". The stress caused by the application of the load to the mounted specimen can be computed, or a high stability stress gauge member can be used to measure the stress directly. The use of a stress gauge member, although it is not necessary, does have the added advantage of also permitting the monitoring of the stress response at the center of the test specimen during temperature cycling or storage.

Accordingly, it is an object of the instant invention to provide a means (such as a device and/or a method) which permits, in a laboratory setting, the ascertainment and evaluation of the stress response of a preselected solid propellant to thermally induced axial compressive or tensile loading conditions which simulate those that would occur in a case-bonded solid rocket grain.

It is another object of this invention to provide the aforementioned stress response ascertainment and evaluation means in the form of analog device which is simple in structure, is economical to manufacture, and is easy to use.

It is still another object of the instant invention to provide in the above-mentioned analog device a unique "strain multiplier" constituent component assembly to produce significant strains, of the type simulating those caused by the aforesaid loading conditions, in a test specimen of the preselected solid propellant.

It is yet another object of this invention to use, in the hereinabove mentioned "strain multiplier", a plurality of laterally-restrained disk-like configured, aligned, and stacked rubber member sandwiched between two (attachment) metal members, such that the volume changes of the rubber disk-like members (which are associated with thermal expansion and contraction) are accomodated by movement (i.e., deflections) in the axial direction, and the movements are approximately three (3) times greater than could be realized from unrestrained rubber members of the same thickness.

It is a further object of the instant invention to provide a novel method of ascertaining and evaluating the stress response of a preselected solid propellant to thermally induced axial compressive or tensile loading conditions which simulate those that would occur in a case-bonded solid rocket grain.

These objects of the instant invention, as well as other objects related thereto (such as reliability of the device and method), will become readily apparent after a consideration of the description of the invention, together with reference to the contents of the figures of the drawing.

DESCRIPTION OF THE DRAWING

FIG. 1 is a side elevation view in simplified schematic and pictorial view, partially fragmented, of a preferred embodiment of the device portion of the instant invention (and, in phantom, of a variation thereof), with a specimen, of the solid propellant to be tested, mounted therein;

FIGS. 2 and 3 are top plan views, in simplified form, of, respectively, the top support plate-like member and the bottom support plate-like member of the frame assembly of the preferred embodbiment, and variation thereof, of the device portion of the instant invention;

FIG. 4 is a side elevation view, in simplified schematic and pictorial form, of a representative one of a plurality of rods of the frame assembly of the preferred embodiment, and of the variation thereof, of the device portion of the instant invention;

FIG. 7 is a side elevation view, in simplified schematic and pictorial form, of the adjustable component of the preferred embodiment, and variation thereof.

Figure 5A:
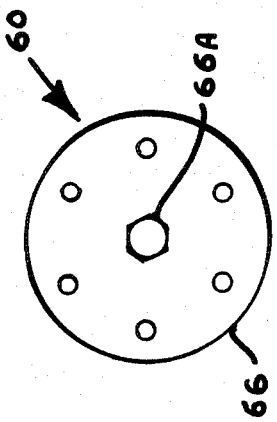
FIGS. 5A and 5B are, respectively, a top plan view and a side elevation view partially in cross-section, in simplified schematic and pictorial form, of one of the major components of the preferred embodiment, and variation thereof, for mounting a test specimen (partially shown, and in phantom) within the aforementioned frame assembly; and, also shown in 5B, in the interest of better orienting the reader, is a stress gauge member of the variation of the preferred embodiment.
Figure 8A:
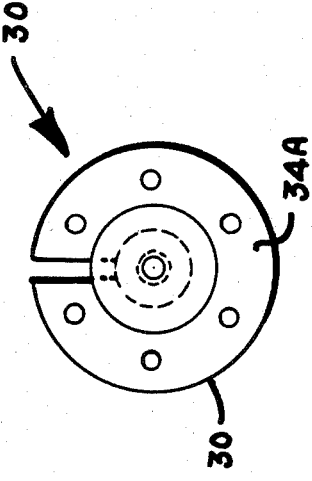
FIGS. 8A and 8B are, respectively, a top plan view and a side elevation view, in simplified schematic and pictorial form, of the base plate component of the variation of the preferred embodiment.

It is here to be noted that the contents of the figures of the drawing also collectively show the result of practicing the steps of the method portion of the invention.

DESCRIPTION OF THE PREFERRED EMBODIMENT

As a preliminary matter, it is to be noted and remembered that the instant invention is a simultaneous incremental strain/incremental temperature analog device (such as preferred embodiment 10, FIG. 1, and variation thereof 10A, FIG. 1) for use with a test specimen (such as solid propellant 100, FIGS. 1 and 5B), and for use with a means (such as temperature conditioning chamber 200, FIG. 1) for subjecting the analog device 10, 10A (with the test specimen 100 mounted therein) to a preselected temperature.

Accordingly, in the most basic and generic structural form, the preferred embodiment 10, FIG. 1, of the inventive simultaneous incremental strain/incremental temperature analog device comprises, in combination: a frame assembly 20, FIGS. 1–4; means (generally designated 30, FIGS. 1, 5A and 5B) for mounting the test specimen 100; the aforementioned "strain multiplier" or, more accurately, means (generally designated 40, FIGS. 1, 6A and 6B), disposed within the frame assembly 20, for permitting the application of a thermally induced axial load, compressive L1 or tensile L2, to the mounted test specimen 100, so that the test specimen could be and is loaded, stressed, and strained; and means (generally designated 50, FIGS. 1 and 7), operably associated with the mounted test specimen 100, for measuring the thermally induced compressive or axial load L1, L2 applied to the mounted specimen 100.

More specifically, the frame assembly 20, FIGS. 1–4, includes: a top support plate-like member 22, FIGS. 1 and 2; a bottom support plate-like member 24, FIGS. 1 and 3; and means (generally designated 26, FIGS. 1 and 4), interposed between the top and bottom support plate-like members 22 and 24, for maintaining the support plate-like members 22, 24 in an aligned, spaced-apart, parallel relationship. As a matter of preference and not of limitation, the top and bottom support-plate members 22, 24 are made of metal, e.g., steel. Also as a matter of preference, the means 26 for maintaining the support plate-like members 22, 24 in an aligned, spaced-apart, parallel relationship includes a plurality (preferably four) of rods 28, FIGS. 1 and 4, of the same length which are made of metal (e.g., steel), and which are releasably connected to the support plate-like members. This releasable connection may be by means of threaded ends of rods 28 and complementarily threaded nuts 28A fitted on corresponding threaded rod ends. The nuts 28A preferably are also made of metal (e.g., steel).

Figure 5B:
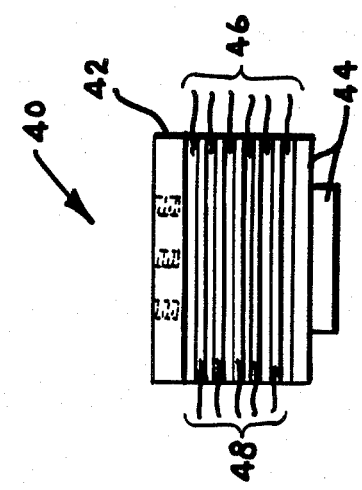
Figure 8B:
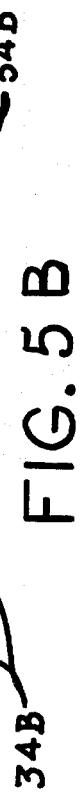

The means 30, operably associated with and disposed within the frame assembly 20, for mounting the test specimen 100 includes: a disk-like member 32, linked to the top support plate-like member 22, FIG. 1, and, a flanged cylinder-like member 34, FIGS. 1, 5A and 5B, linked to the bottom support plate-like member 24. When the test specimen 100 is mounted, as is shown in FIGS. 1 and 5B, it is disposed between, and in contact with, the lower surface 32B of the disk-like member 32 and the upper surface 34A of the flanged cylinder-like member 34. As a matter of preference, the two mounting members 32 and 34 are made of metal (e.g., steel), and the test specimen 100 is mounted on members 32 and 34 by adhesive bonding.

Figure 6A:
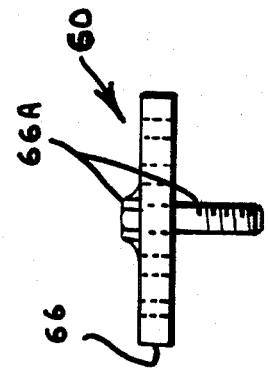
FIGS. 6A and 6B are, respectively, a top plan view and a side elevation view, in simplified schematic and pictorial form, of the aforementioned "strain multiplier" constituent component assembly of the preferred embodiment, and variation thereof.
Figure 6B:
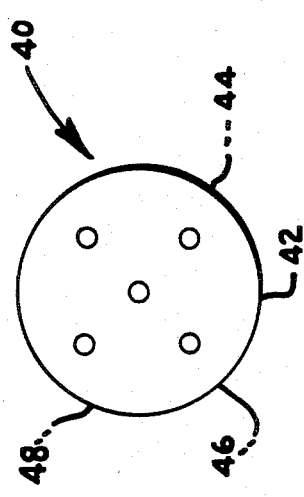

The "strain multiplier" or, more accurately, the means 40, FIGS. 1, 6A and 6B, for permitting the application of a thermally induced axial load, such as compressive load L1 or tensile load L2, to the test mounted test specimen 100 to load, stress, and strain the test specimen 100, includes: a metal upper attachment plate member 42 captured within the frame assembly 20 and releasably attached (preferably by a plurality of cap screws, such as 5 of them) to the bottom surface 22B of the top support plate-like member 22, FIGS. 1 and 2; a metal lower attachment double cylinder-like member 44 captured within the frame assembly 20 and aligned with, and below of, the upper attachment plate member 42; a plurality of similarly configured, sized, and aligned disk-like rubber members 46 captured within the frame assembly 20, between and in contact with, the metal upper attachment plate member and the metal lower attachment double cylinder-like member, with each rubber disk-like member 46 having a diameter-to-thickness ratio greater than thirteen (13), a ratio which has been found to be critical; and, a plurality of similarly configured, sized, and aligned disk-like metal members 48, of the same size as the disk-like rubber members 46, disposed such that a stack of the rubber members 46 and of the metal members 48 in a sandwiched condition is formed, with a rubber member 46 positioned at the top of the stack, and with another rubber member 46 positioned at the bottom of the stack, and also with the stack as a whole being sandwiched between the metal upper and lower attachmemt members 42, 44.

As a matter of preference and not of limitation, the metal attachmemt members 42, 44 and the disk-like metal members 46 are made of aluminum or steel; and the constituent components of the stack 42, 46, 48 and 44 are adhesively bonded as a stack.

The means 50, FIGS. 1 and 7, for measuring the thermally induced axial loads, compressive load L1 and tensile load L2, that are applied to the test specimen 100 mounted in the analog device 10, 10A includes a conventional commercially-available load cell member 52 (such as an "Interface", Model No. 1420-AF, rated for ±250 pounds), FIG. 1, which is interposed between, and is removably attached to, the lower attachment double cylinder-like member 44 of the "strain multiplier" means 40 and the disk-like member 32 of the test specimen mounting means 30. This load measuring means 50 further includes an adjustable coupling (such as 54, FIGS. 1 and 7) which is disposed between, and interconnects, the load cell member 52 and the disk-like member 32 of the test specimen mounting means 30. The load measuring means 50 is, of course, operably associated with the test specimen 100 when the specimen is mounted in the analog device 10, 10A.

The variation 10A, FIGS. 1, 5B, 8A and 8B, of the analog device 10 is structurally similar to the preferred embodiment 10 in that the variation 10A includes all of the structure of the preferred embodiment 10, and in addition further includes a means (generally designated 60, FIGS. 1, 5B, 8A and 8B), which is operably associated with the mounted test specimen, for measuring the stress response at the center of the test specimen 100 to the thermally induced axial load, either compressive L1, or tensile L2. This stress response measuring means 60 includes: a liner member 62, FIGS. 1 and 5B, but best seen in FIG. 5B, which is interposed between, and is in contact with, the upper surface 34A of the flanged cylinder-like member 34 of the test specimen mounting means 30, and the lower surface of the mounted test specimen 100; a conventional commerically-available stress gauge member 64 (such as a "Senso-Metrics", Model 601358-14 rated for ±25 psig), FIGS. 1 and 5B, but best seen in 5B, which is releasably retained (preferably by a retaining nut 68A, FIG. 5B) in a vertically aligned position (preferably by an alignment ring 68B, FIG. 5B) within the flanged cylinder-like member 34 of the test specimen mounting means 30, and with the stress gauge member 64 being in contact with the lower surface of the liner member 62 at a location beneath the center of the lower surface of the mounted test specimen 100; and, a base plate member 66, FIGS. 1, 8A and 8B, but best seen in FIGS. 8A and 8B, interposed between and in contact with the upper surface 24A of the bottom support plate-like member 24 of the frame assembly 20 (best seen in FIG. 1) and the lower surface 34B of the double cylinder-like member 34 of the test specimen mounting means 30. As a matter of preference, the base plate member 66 is made of metal (e.g., steel); and, the base plate member 66 has a centrally located bolt 66A, FIGS. 8A and 8B, for removably attaching the base plate member 66 to the bottom support plate-like member 24 of the frame assembly 20.

DESCRIPTION OF THE INVENTIVE METHOD

The method portion of the instant invention (i.e., the method of ascertaining and evaluating the stress response of a preselected solid propellant 100 to thermally induced loading conditions, compressive L1 and L2, which simulate the loading conditions in a case-bonded solid rocket grain) essentially comprises the below listed steps:

Firstly, inventing a test specimen 100 of the preselected solid propellant, while in a stress-free temperature condition, in the simultaneous incremental strain-/incremental temperature analog device 10, or variation thereof 10A, hereinbefore described and shown.

Next, applying a preselected temperature to the analog device 10, 10A and to the test specimen 100 mounted therein, by any suitable means, such as by use of the conventional, commercially available "Aminco" temperature conditioning chambers 200, FIG. 1. As a result, the laterally restrained disk-like rubber members 46 of the "strain multiplier" 40 undergo volume changes due to thermal expansion (if the preselected temperature is increased) or contraction (if the preselected temperature is decreased), and the test speciman thereby is subjected to thermally induced axial compression loading L1 (when the temperature is increased and the rubber expands) and thermally induced tensile loading L2 (when the temperature is decreased and the rubber contracts). It is here to be noted that these thermally induced loading conditions simulate the loading condition that would occur in a case-bonded solid rocket grain of the solid propellant test specimen.

Then, ascertaining from the load cell member 52, FIGS. 1 and 5B, the amount of thermally induced axial compressive or tensile load L1, L2 being applied (at that temperature) to the solid propellant test specimen. When the applied load is measured, the resultant stress response (i.e., stress) of the solid propellant test specimen 100 to this thermally induced axial compressive or tensile applied load (which simulates the axial compressive or tensile loading condition which would occur in a case-bonded solid rocket grain of the solid propellant test specimen) can be determined (i.e. calculated) and evaluated.

However, if the variation 10A of the preferred embodiment 10 of the inventive analog device is used, then the hereinbefore method includes an additional step which eliminates determining (i.e. calculating) the resulting stress. That step, which is performed after the step of ascertaining from the load cell member 52 the amount of the thermally induced loading being applied, comprises ascertaining from the stress gauge member 66 the resulting stress (i.e., the stress response) which can then be evaluated.

It is to be noted that irrespective of whether the preselected temperature to be attained and applied is higher than, or lower than, the stress-free temperature, the preselected temperature can be attained and applied either at a constant rate, or at a variable rate (such as in steps at regular time intervals).

MANNER AND USE OF THE INVENTION

The manner of use, and of operation, of the preferred embodiment 10, and of the variation 10 thereof, of the device portion (i.e., the analog device) of the instant invention can be easily ascertained by any person of ordinary skill in the art from the foregoing description, coupled with reference to the contents of the Figures of the drawing.

For those not of the art, the manner of use and operation of the analog device 10, 10A portion of the instant invention can be learned by correlating the essential and fundamental steps of the described method portion of the invention with the contents of the Figures of the drawing and with the description of the preferred embodiment 10, and variation 10A, of the instant invention.

CONCLUSION

It is abundantly clear from all of the foregoing, and from the contents of the Figures of the drawing, that the stated objects of the instant invention, as well as other objects related thereto, have been achieved.

It is to be noted that, although there have been described and shown the fundamental and unique features of the device portion of the instant invention as applied to a preferred embodiment 10, and a variation 10A of it, nevertheless various other embodiments, variations, adaptions, substitutions, additions, omissions, and the like may occur to and can be made by those of ordinary skill in the art. For example, the configuration of the top and bottom support plate-like members 22, 24 could be round, oval, or triangular, rather than square or rectangular.

It is also to be noted that, because of the teachings herein, it may occur to others of ordinary skill in the art that, in appropriate particular circumstances, the number of the basic and fundamental steps of the inventive method portion of the instant invention can be increased, decreased or otherwise varied, and/or that their sequence can be changed. For example, the presently described first step of the method portion of the instant invention could be divided into two separate and distinct steps, such as: Firstly, mounting a test specimen of said preselected solid propellant in a simultaneous incremental strain/incremental temperature analog device, wherin said analog device comprises: etc; and, secondly, adjusting (i.e., tightening or loosening) the frame assembly 20 of the analog device such that said mounted specimen is in a stress-free temperature condition. In this regard, it is to be noted and remembered that, in spite of any variations in the number or sequence of the steps of the particular method set forth herein, only the same results (as already described herein) will be obtained.

What is claimed is:

1. A simultaneous incremental strain/incremental temperature analog device for use with a test specimen, and for use with a means for subjecting said analog device, with said test specimen mounted therein, to a preselected temperature, said analog device comprising:
   a. a frame assembly, said frame assembly including a top support plate-like member, a bottom support plate-like member, means, interposed between said top and bottom support plate-like members, for maintaining said support plate-like members in an aligned, spaced-apart, parallel relationship;
   b. means, operably associated with and disposed within said frame assembly, for mounting said test specimen;
   c. means, operably associated with and disposed within said frame assembly, for permitting the application of a thermally induced axial compressive or tensile load to said test specimen when said specimen is mounted, whereby said mounted specimen can be loaded, stressed, and strained; and
   d. means, operably associated with said test specimen when said specimen is mounted, for measuring said thermally induced axial compressive or tensile load applied to said mounted specimen;
   whereby, when said test specimen is mounted in said analog device, and when said analog device and said test specimen mounted therein are subjected to said preselected temperature, the stress response of said mounted test specimen to the thermally induced axial compressive or tensile load conditions caused by said preselected temperature, can be ascertained and evaluated.

2. A simultaneous incremental strain/incremental temperature analog device, as set forth in claim 1, wherein said means, of said frame assembly, for maintaining said support plate-like members in an aligned, spaced-apart, parallel relationship includes a plurality of rods of the same length.

3. A simultaneous incremental strain/incremental temperature analog device, as set forth in claim 2, wherein said plurality of rods of the same length are releasably connected to said aligned, spaced-apart, parallel positioned top and bottom support plate-like members.

4. A simultaneous incremental strain/incremental temperature analog device, as set forth in claim 3, wherein said top support plate-like member, said bottom support plate-like member, and each of said plurality of rods of the same length are made of metal.

5. A simultaneous incremental strain /incremental temperature analog device, as set forth in claim 4, wherein said means, operably associated with and disposed within said frame assembly, for mounting said test specimen within said frame assembly includes:
   a. a disk-like member linked to said top support plate-like member; and
   b. a flanged cylinder-like member linked to said bottom support plate-like member;

with said test specimen, when it is mounted, being disposed between, and in contact with, the lower surface of said disk-like member and the upper surface of said flanged cylinder-like member.

6. A simultaneous incremental strain/incremental temperature analog device, as set forth in claim 5, wherein said disk-like member linked to said top support plate-like member, and said flanged cylinder-like member linked to said bottom support plate-like member, are made of metal.

7. A simultaneous incremental strain/incremental temperature analog device, as set forth in claim 6, wherein said means, operably associated with and disposed within said frame assembly, for permitting the application of a thermally induced axial compressive or tensile load to said test specimen when said test specimen is mounted, whereby said test specimen can be loaded and stressed, includes:
 a. a metal upper attachment plate member captured within said frame assembly and releasably attached to said top support plate-like member;
 b. a metal lower attachment double cylinder-like member captured within said frame assembly and aligned with and below said upper attachment plate member;
 c. a plurality of similarly configured, sized, and aligned disk-like rubber members captured within said frame assembly, between and in contact with, said metal upper attachment plate member and said metal lower attachment double cylinder-like member, wherein each rubber disk-like member has a diameter-to-thickness ratio greater than thirteen;
 d. a plurality of similarly configured, sized, and aligned disk-like metal members, of the same size as said disk-like rubber members, disposed such that a different one of said disk-like metal members is interposed between and is in contact with every two adjacent disk-like rubber members, whereby a stack of said rubber and said metal disk-like members in a sandwiched condition is formed, with a rubber member positioned at the top of said stack, and with another rubber member positioned at the bottom of said stack, and also with said stack being sandwiched between said metal upper and lower attachment members, whereby said stack and said constituent disk-like rubber member and metal members are laterally restrained.

8. A simultaneous incremental strain/incremental temperature analog device, as set forth in claim 7, wherein said means for measuring said thermally induced axial compressive or tensile load applied to said test specimen includes a load cell member interposed between and removably attached to said lower attachment cylinder-like member of said means for permitting the application of a thermally induced axial compressive or tensile load, and said disk-like member of said means for mounting said test specimen.

9. A simultaneous incremental strain/incremental temperature analog device, as set forth in claim 8, wherein said means for measuring said thermally induced axial compressive or tensile load applied to said test specimen further includes an adjustable coupling disposed between and interconnecting said load cell member and said disk-like member of said means for mounting said test specimen.

10. A simultaneous incremental strain/incremental temperature analog device, as set forth in claim 9, wherein said analog device further comprises means, operably associated with said test specimen when said specimen is mounted, for measuring the stress response at the center of said test specimen to said thermally induced axially applied compressive or tensile load.

11. A simultaneous incremental strain/incremental temperature analog device, as set forth in claim 10, wherein said means for measuring stress response at the center of said test specimen includes:
 a. a liner member interposed between and in contact with the upper surface of said cylinder-like member of said means for mounting said test specimen and the lower surface of said test specimen when said test specimen is mounted; and
 b. a stress gauge member releasably retained within said flanged cylinder-like member of said means for mounting said test specimen, with said stress gauge member in contact with the lower surface of said liner member at a location beneath the center of the lower surface of said test specimen.

12. A simultaneous incremental strain/incremental temperature analog device, as set forth in claim 11, wherein said analog device further includes a base plate member interposed between and in contact with the upper surface of said bottom support plate-like member of said frame assembly and the lower surface of said double cylinder-like member of said means for mounting said test specimen.

13. A simultaneous incremental strain/incremental temperature analog device, as set forth in claim 12, wherein said base plate member is made of metal.

14. A simultaneous incremental strain/incremental temperature analog device, as set forth in claim 9, wherein:
 a. said test specimen is a solid propellant; and
 b. said thermally induced axial compressive or axial loading conditions simulate those that would occur in a case-bonded solid rocket grain.

15. A simultaneous incremental strain/incremental temperature analog device, as set forth in claim 14, wherein said solid propellant test specimen, when it is mounted, is disposed between, and is bonded to, the lower surface of said disk-like member of said test specimen mounting means and the upper surface of said double cylinder-like member of said test specimen mounting means.

16. A method of ascertaining and evaluating the stress response of a preselected solid propellant to thermally induced axial compressive or tensile loading conditions which simulate those that would occur in a case-bonded solid rocket grain, comprising the steps of:
 a. mounting a test specimen of said preselected solid propellant in a stress-free temperature condition in a simultaneous incremental strain/incremental temperature analog device, wherein said analog device comprises:
  (1) a frame assembly which includes: a top support plate-like member; a bottom support plate-like member; and a plurality of rods of the same length interposed between and releasably connected to said plate-like members, whereby said plate like members are maintained in an aligned, spaced-apart, parallel relationship to each other;
  (2) means, operably associated with and disposed within said frame assembly, for mounting said test specimen within said frame assembly;
  (3) means, operably associated with said mounted test specimen, and disposed within said frame assembly and above said test specimen mounting means, for permitting the application of a thermally induced axially compressive or tensile load to said mounted specimen, and thereby axially loading and stressing said mounted test specimen, wherein this means includes:
- an upper attachment metal plate member removably attached to said top support plate-like member of said frame assembly;
- a lower attachment metal cylinder-like member aligned below said upper attachment metal plate member in parallel spaced-apart relationship therewith;
- a plurality of similarly configured, sized, and aligned disk-like rubber members captured within said frame assembly between, and in contact with, said lower and upper attachment members, wherein each rubber member has a diameter-to-thickness ratio greater than thirteen; and
- a plurality of similarly configured, sized, and aligned disk-like metal members, of the same size as said disk-like rubber members, disposed such that a different one of said disk-like metal members is interposed between and is in contact with every two adjacent disk-like rubber members, whereby a stack of such rubber and said metal disk-like members is formed, with a rubber member positioned at the top of said stack, and with another rubber member positioned at the bottom of said stack, and also with said rubber and said metal disk-like members disposed in a sandwiched condition, and whereby said stack and said constituent disk like rubber members and metal members are laterally restrained;

(4) means, operatively associated with said mounted test specimen, for measuring a thermally induced axial compressive or tensile load applied to said mounted test specimen, wherein this means includes:
- a load cell member interposed between and removably attached to said lower attachment cylinder-like member of said means for permitting the application of a thermally induced axial compressive or tensile load, and said disk-like member of said means for mounting said test specimen; and
- an adjustable coupling disposed between and interconnecting said load cell member and said disk-like member of said means for mounting said test specimen;

b. applying a preselected temperature to said analog device and to said solid propellant test specimen mounted in said analog device, whereby said laterally restrained rubber disk-like members of said analog device undergo volume changes due to thermal expansion and contraction, with said preselected solid propellant test specimen being thereby subjected to thermally induced axial compressive or tensile loading conditions which simulate those that would occur in a case-bonded solid rocket grain; and c. ascertaining from said load cell member the amount of thermally induced axial compressive or tensile load being applied to said solid propellant test specimen;

whereby the stress response of said preselected solid propellant to said thermally induced axial compressive or tensile loads, which simulate those axial compressive or tensile loading conditions which would occur in a case-bonded solid rocket-grain, can be ascertained and evaluated.

17. A method, as set forth in claim 16, wherein said preselected solid solid propellant test specimen has a known stress-free temperature, and said preselected temperature, applied during the step of applying a preselected temperature to said analog device and to said solid propellant test specimen mounted therein, is a temperature lower than said known stress-free temperature, whereby said rubber disk-like members contact, and thereby said solid propellant test specimen is subjected to a thermally induced axial tensile loading condition which simulates such a loading condition in a case-bonded solid rocket grain.

18. A method, as set forth in claim 17, wherein said lower preselected temperature is attained and applied at a constant rate.

19. A method, as set forth in claim 17, wherein said lower preselected temperature is attained and applied in steps at regular time intervals.

20. A method, as set forth in claim 16, wherein said preselected solid propellant test specimen has a known stress-free temperature, and said preselected temperature, applied during the step of applying a preselected temperature to said analog device and to said solid propellant test specimen mounted therein, is a temperature higher than said known stress-free temperature, whereby said rubber disk-like members expand, and thereby said solid propellant test specimen is subjected to a thermally induced axial compressive loading condition which simulates such a loading condition in a case-bonded solid propellant grain.

21. A method, as sewt forth in claim 20, wherein said higher preselected temperature is attained and applied at a constant rate.

22. A method, as set forth in claim 20, wherein said higher preselected temperature is attained and applied in steps at regular time intervals.

* * * * *